United States Patent [19]

Beattie et al.

[11] 4,207,323

[45] Jun. 10, 1980

[54] 6-SUBSTITUTED METHYL PENICILLINS, DERIVATIVES AND ANALOGUES THEREOF

[75] Inventors: Thomas R. Beattie, North Plainfield; Frank P. Dininno, Old Bridge; Burton G. Christensen, Metuchen, all of N.J.

[73] Assignee: Merck & Co., Inc., Rahway, N.J.

[21] Appl. No.: 901,867

[22] Filed: May 1, 1978

Related U.S. Application Data

[63] Continuation-in-part of Ser. No. 808,940, Jun. 22, 1977, abandoned, which is a continuation of Ser. No. 634,083, Nov. 21, 1975, abandoned.

[51] Int. Cl.$^2$ .................... A61K 31/38; C07D 499/00
[52] U.S. Cl. .................................. 424/270; 260/245.2; 260/245.3; 548/324; 424/273 R; 424/271
[58] Field of Search ................... 260/306.7 C, 307 A; 548/324; 424/270, 273 R, 271

[56] References Cited

U.S. PATENT DOCUMENTS

| 3,174,964 | 3/1965 | Hobbs et al. | 260/306.7 C |
| 3,809,700 | 5/1974 | Rapoport | 260/306.7 C |
| 4,000,154 | 12/1976 | Gleason et al. | 548/324 |

*Primary Examiner*—Donald G. Daus
*Assistant Examiner*—James H. Turnipseed
*Attorney, Agent, or Firm*—Frank M. Mahon; Julian S. Levitt; Rudolph J. Anderson, Jr.

[57] ABSTRACT

Disclosed are antibiotic 6-(substituted methyl) penicillins, derivatives and nuclear analogues thereof; wherein the methyl substituent is, inter alia, hydroxyl, ketonic oxygen, imino nitrogen, amino or thio. Also disclosed are processes for the preparation of such compounds and their pharmaceutically acceptable salt, ester and amide derivatives; pharmaceutical compositions comprising such compounds; and methods of treatment comprising administering such compounds and compositions when an antibiotic effect is indicated.

3 Claims, No Drawings

6-SUBSTITUTED METHYL PENICILLINS, DERIVATIVES AND ANALOGUES THEREOF

This application is a continuation-in-part of U.S. patent application Ser. No. 808,940, filed June 22, 1977, now abandoned which is a continuation of U.S. patent application Ser. No. 634,083, filed Nov. 21, 1975, now abandoned.

BACKGROUND OF THE INVENTION

This invention relates to a new class of antibiotics which may be generically represented by the following structural formula (I):

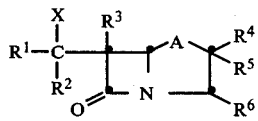

wherein A is S, O, SO, or $NR^7$ ($R^7$ is selected from the group consisting of hydrogen, alkyl, formyl, acyl, thioacyl, alkyl sulfonyl and aryl sulfonyl); X is OH, =O, SH, or =NH, $NH_2$, $NHR^7$; $R^1$ and $R^2$ are independently selected from the group consisting of hydrogen; substituted and unsubstituted: alkyl, aryl, aralkyl, heteroaryl and heteroaralkyl (mono- and bicyclic) wherein the heterocyclic moiety comprises 4–10 ring atoms and the hetero atom (or atoms) is O, N or S; and wherein the ring or chain substituent is selected from: amino, carboxy, hydroxy, alkoxy, carbalkoxy, lower alkyl, heteroaryl, and substituted amino such as mono- and dialkylamino, and acylamino; and perhaloalkyl; with the proviso that, when X is =O or =NH, the substituent $R^2$ is absent; examples of such substituents $R^1$ and $R^2$ are methyl, trifluoromethyl, phenyl, substituted phenyl, benzyl and the like; $R^3$ is selected from the group consisting of hydrogen, alkoxy, halogen, such as fluoro and bromo and alkylthio; $R^4$ and $R^5$ are independently selected from the group consisting of hydrogen, and alkyl and $R^6$ is $COXR^8$, wherein X is oxygen or sulphur and $R^8$ is conventionally known in the penicillin and penicillin-like art and is, inter alia, representatively selected from the group consisting of hydrogen, trialkylsilyl, and the pharmaceutically acceptable salt, ester and amide moieties known in the art such as sodium, potassium, pivaloyloxymethyl, and the like.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms—they are generally not effective against a broad range of pathogens.

Unexpectedly, it has been found that the compounds of the present invention are broad spectrum antibiotics, which are useful in animal and human therapy and in inanimate systems. It will be recognized from the above generic representation (I) that the principal novel feature of the compounds of the present invention is the 6-substituted methyl substituent, which position heretofore in the penicillin art has always been amino or substituted amino for compounds of high activity. It will also be noted, except where expressly stated, that the balance of the penicillin or penicillin-like structure (I) is well-known in the relevant art.

Thus, it is an object of the present invention to provide a novel class of antibiotics which includes, inter alia, species having the basic nuclear structure of the penicillins but which are characterized by having a substituted methyl substituent at the 6-position of the β-lactam ring. These antibiotics are active against a broad range of pathogens which representatively include both gram positive bacteria such as *Staphylococcus aureus* and *Streptococcus pyogenes* and gram negative bacteria such as *E. coli* and *Klebsiella pneumoniae*. Further objects of this invention are to provide chemical processes for the preparation of such antibiotics; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are conveniently prepared from the known basic nucleus II:

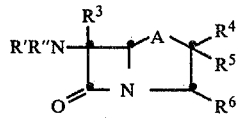

wherein all substituents are as previously defined and R' and R" are independently selected from hydrogen or an acyl radical, known in the art.

With reference to structure I, above-given, the preferred embodiments of the present invention are those wherein:

A is selected from the group consisting of S, O, SO and $NR^7$; ($R^7$ is hydrogen, $C_1$–$C_6$ loweralkyl, $C_1$–$C_6$ loweralkanoyl or acyl), X is selected from the group consisting of OH, SH, =O, =NH, $NH_2$ and $NHR^7$; $R^1$ and $R^2$ are independently selected from the group consisting of hydrogen, lower alkyl having from 1 to 6 carbon atoms, aralkyl such as benzyl and phenethyl, heteroaralkyl, perfluoroalkyl, such as trifluoromethyl, and aryl such as phenyl and ring substituted aryl and ring and chain substituted aralkyl wherein the substituent is selected from the group consisting of lower alkyl, halogen such as Cl, Br, I or F, alkoxy, amino, carboxy, cyano, hydroxyl and the like; $R^3$ is hydrogen, alkoxy such as methoxyl; bromo, fluoro and lower alkylthio; $R^4$ and $R^5$ are independently selected from the group consisting of hydrogen, and lower alkyl having from 1 to 6 carbon atoms. $R^6$ is $COXR^8$ wherein X is oxygen or sulphur and $R^8$ represents an ester moiety derived, for example, from alcohols, mercaptans and thio phenols.

For example, $R^8$ can be alkyl having 1–10 carbon atoms, straight or branched, such as methyl, ethyl, t-butyl, pentyl, decyl, etc.; substituted alkyl, wherein the alkyl portion has 1–10 carbon atoms but is preferably methyl or ethyl; and the substituent can be a heterocyclic structure having 1–3 hetero atoms of either, O, N, or S; such as phthalimidomethyl, succinimidomethyl, phenacyl, p-bromophenacyl, (2-thienyl)methyl, (6-indenyl)methyl, acetoxyacetylmethyl, carboxymethyl, ethoxyethoxyethyl, (2-methylamino)ethyl, (2-diethylamino)ethyl, 2-(p-methylphenyl)sulfonylethyl, 2-(p-methylphenyl)ethyl, (2-acetamido)ethyl, etc. The substituent on the alkyl group can also be carboxyl, e.g., $R^8$ is α-carboxy-β,β-dimethylpropyl; alkoxyalkyl wherein the alkoxy portion has 1–10 and preferably 1–6 carbon atoms, but can be branched, straight, or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl, etc.; alkanoyloxyalkyl wherein the alkanoyloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, etc.; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, etc.; alkenyl having 1-10 carbon atoms, either straight or branched, e.g., allyl, 2-propenyl, 3-butenyl, 4-pentenyl, 2-butenyl, 3-pentenyl, 2-methyl-2-propenyl, methallyl, etc.; alkynyl having 1-10 carbon atoms, either straight or branched, e.g., 3-pentynyl, propargyl, ethynyl, etc.; alkanoyl, either straight or branched, having 1-10 carbon atoms, such as pivaloyl, acetyl, propionyl, etc.; aralkyl wherein alkyl has 1-3 carbon atoms, such as benzyl, benzhydryl, and substituted benzyl or benzhydryl, e.g., o-nitrobenzyl, 3,5-dinitrobenzyl, p-methoxybenzyl, p-nitrobenzyl, 3,5-dichloro-4-hydroxybenzyl, p-methoxybenzhydryl, p-carboxybenzyl, the latter being either the free acid or the sodium salt, 2,4,6-trimethylbenzyl, p-(sodiumcarboxylate)benzyl, p-methylbenzyl, or phenylethyl, 2-(p-methylphenyl)ethyl, p-t-butylbenzyl, m-phenoxybenzyl, p-pivaloxyloxybenzyl, and the arylthioalkyl analogues; aryloxyalkyl wherein aryl is preferably a phenyl ring having 0-3 substituents, preferably 0 or 1 substituents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)-phenoxymethyl, (2-methoxy)phenoxymethyl, (1-phenoxy)ethyl, (4-amino)phenoxymethyl, (4-methoxy)-phenylthiomethyl, (4-chloro)phenylthiomethyl, phenylthioethyl; aryl wherein aryl is phenyl or substituted phenyl having 0-3 substituents, preferably 0 or 1 substituent in the ortho or para position, e.g., (4-methyl)phenyl, (4-hydroxy)phenyl; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)-benzyloxymethyl; alkylthioalkyl wherein the alkylthio portion has 1-10 and preferably 1-6 carbon atoms, but can be branched, straight, or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl, etc.; or monocyclic aryl wherein aryl is phenyl, or substituted phenyl such as p-nitrophenyl, 3,5-dinitrophenyl, or p-carboxyphenyl, the latter having either the free acid or the sodium salt form.

In addition to the esters listed above, amides can also be employed, i.e., wherein X is the

groups, and $R^8$ is as defined.

Particularly preferred esters are those in formula I wherein X is oxygen and $R^8$ is aralkyl, aryloxyalkyl, aralkoxyalkyl, alkylthioalkyl, haloalkyl, or alkenyl.

It will be apparent from a further reading of this application that in many of the chemical reactions described, the penicillin is blocked at position 3 by a so-called "easily removable blocking group". Many of these groups are contained within the above definition of the chain —$COXR^8$ in formula I. However, we have found it more convenient to use only relatively a few of these groups during such chemical reactions, then to remove the group to the free acid, and subsequently to react the latter with the desired alcohol to yield the suitable ester.

In this connection, it is noted that preferred "blocking groups" include the sub-generic groups defined above as aralkyl, haloalkyl, alkanoyloxyalkyl, alkoxyalkyl, alkenyl, substituted alkyl, or aralkoxyalkyl, and also include mono-, di-, and tri-alkylsilyl, wherein alkyl has 1-10 carbon atoms.

More specifically, preferred "blocking groups" include benzyl, phenacyl, methoxymethyl, trichloroethyl, trimethylsilyl, benzoylmethyl, p-nitrobenzyl, p-bromophenyl, p-bromophenacyl, p-methoxybenzyl, benzhydryl. These blocking groups are preferred since they are generally recognized easily-removable blocking groups in cephalosporin and penicillin art. Although we describe procedures for the removal of these blocking groups, such processes are considered within the skill of those in the art.

On the other hand, the novel penicillins of this invention are best utilized pharmacologically as either the free acid in the form of commonly used, nontoxic pharmaceutically acceptable salts, or certain of the above listed esters. For instance, esters belonging to the groups defined as aralkyl, alkylthioalkyl, or alkenyl yield final products having outstanding oral activity. More specifically, high oral activity of the novel penicillins is obtained when $R^8$ is (2-methylthio)ethyl, benzyl, pivaloyloxymethyl, 3-phthalidyl, p-t-butylbenzyl, p-pivaloyloxybenzyl, m-phenoxybenzyl, benzyl, or 3-buten-1-yl.

By the term "non-toxic pharmaceutically acceptable salts" is meant salts that are suitable for isolating, purifying and/or marking purposes, for example, salts with bases or with acids, as well as inner salts. Salts with bases are in the first place metal salts, especially alkali metal salts, for example, sodium or potassium salts, or alkaline earth metal salts, for example magnesium or calcium salts, or ammonium salts, including ammonium salts with organic bases such as tri-lower alkyl-amines, for example, trimethylamine or triethylamine, or N-lower alkylazacycloalkanes, for example, 1-methyl-pyrrolidine or 1-ethyl-piperidine, also dibenzylethylenediamine or procaine. They are obtained, for example, by treating the free compounds or inner salts with the basic compounds, as desired with the acid of an ion exchange resin.

Acid addition salts are in the first place those with strong inorganic acids, such as hydrochloric, hydrobromic or sulphuric acid, or with strong organic acids such as strong organic sulphonic acids, for example, methanesulphonic, 2-hydroxyethanesulphonic or p-toluenesulphonic acid, or with a strong organic carboxylic acid, for example, trifluoroacetic acid. They can be obtained, for example, by treating the free compounds with the appropriate strong acids, if desired with the aid of an ion exchange resin.

Inner salts, which appear as hybrid ions, are obtained by treating an acid addition salt with an appropriate, weakly basic ion exchange resin, or by titrating with a base up to the isoelectric point, or from a salt with a base by treatment with an acid.

The most preferred embodiments of the present invention are those wherein:

A is S, O, or SO;

X is OH;

R¹ and R² are independently selected from the group consisting of hydrogen, substituted and unsubstituted lower alkyl having from 1-6 carbon atoms; ring and chain substituted aryl, aralkyl and heteroaralkyl such as phenyl, benzyl, phenethyl, 1-hydroxy-, 1-amino-, 1-carboxy-ethylbenzene, thienylmethyl and the like; wherein the ring and chain substituents are selected from the group consisting of COOH, NH₂, OH and the like;

R³ is hydrogen or methoxyl;

R⁴ and R⁵ are independently selected from the group consisting of hydrogen, and methyl; and R⁶ is COXR⁸, wherein X and R⁸ are as defined above.

In general the compounds of the present invention are prepared according to the following reaction scheme:

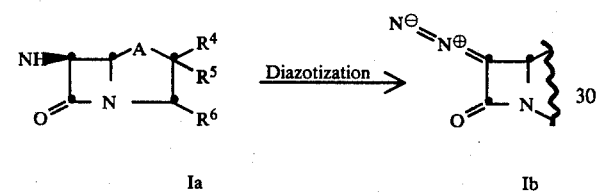

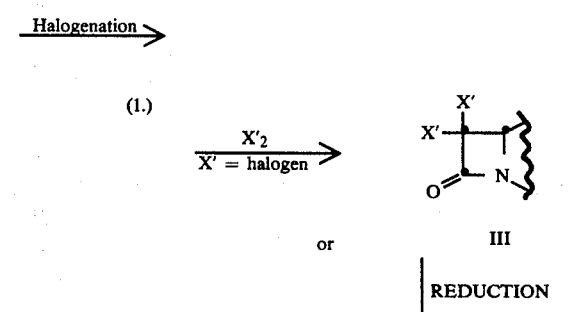

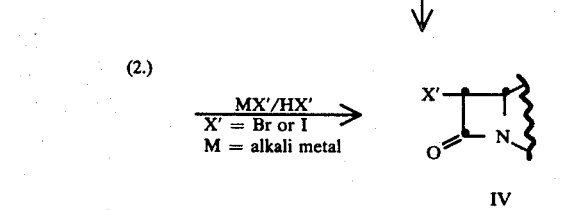

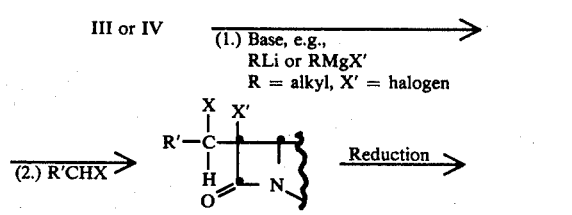

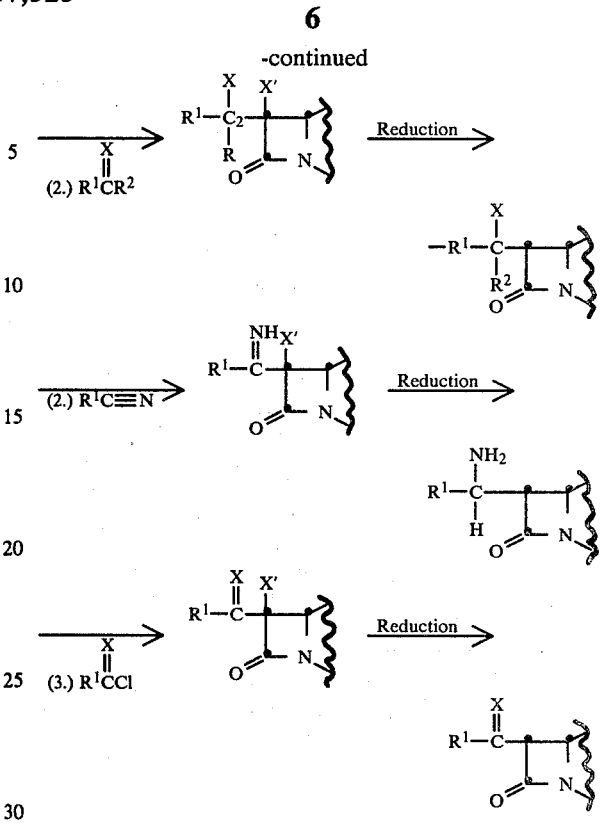

In words relative to the above reaction diagram, the free 6-amino species, Ia, is diazotized by conventional procedures such as by reaction with NaNO₂ in the presence of acid such as p-toluenesulfonic acid in a solvent such as methylene chloride or the like at a temperature of from 0° to about 25° C. for from a few minutes to 4 hours. The resulting diazo derivative, Ib, isolated by conventional procedures such as extraction followed by organic solvent removal, is then halogenated by either of two procedures. Both are well-known. The first procedure provides the 6,6,-dihalo species, III, and involves direct halogenation, such as bromination, in a solvent such as methylene chloride or the like at a temperature of from −78° C. to about 0° C. for from a few mins. to about 4 hours. The second procedure provides the mono halo species, IV, preferably the 6-iodo or 6-bromo species and is conducted in a polar solvent such as water, acetone, alcohol or aqueous mixtures thereof in the presence of the halide salt and its corresponding acid. The reaction is conducted at from 0° to about 25° C. for from a few mins. to 4 hours. Products, III and IV, if desired are separated by conventional procedures involving solvent extraction, concentration, and chromatography. It should be noted that III is convertible to IV by reduction. A particularly suitable reduction is effected by a Zn-Ag couple in methanol according to reported procedures such as R. D. Clark and C. H. Heathcock, J. Org. Chem., 38, 3658 (1973); alternatively catalytic hydrogenation employing Pd/C, Pd/CaCO₃ or PtO₂ in solvents such as alcohol, ethylacetate, or dioxane at 0° C. to about 25° C. under 1-50 atmospheres of hydrogen.

Intermediate products, III and IV, are converted to the final products of the present invention by contacting either with a base such as an organo metallic base such as a lithium alkyl or a Grignard reagent, RMgX', wherein R is alkyl, aryl or the like and X' is halogen such as bromo and thereafter adding to the reaction mixture the reagent of choice to give the desired final product. The reagents, as shown in the diagram are: $H_2CO$; $R^1CHX$, $R^{1X}CR^2$, $R^{1X}CCl$, and $R^1C≡N$; wherein $R^1$ and $R^2$ are as defined above, and X is oxygen or sulphur. Typically the reaction is conducted in a solvent such as tetrahydrofuran, ether, dimethoxyethane or mixtures thereof or the like at a temperature of from $-100°$ to about $0°$ C. for from a few minutes to about 4 hours. Typically, the base is added first. Products derived from the 6,6-dihalo species, III, yield the illustrated halohydrins which are reduced to the final products, I, by conventional techniques such as zinc-silver couple in methanol or hydrogenation.

It is to be noted that the above reaction scheme is no regio-specific for the 6-position and that there are no criticalities of reaction parameters other than those set forth above and elaborated upon in the following specific examples. It should be further noted that the above-described procedure provides all embodiments of the present invention except those wherein $R^3$ is other than hydrogen. When $R^3$ is alkoxyl or alkylthio such as methoxyl or methylthio, for example, the above procedure is modified by a subsequent procedure which involves derivatization of the 6-substituted methyl species to form those species of the present invention wherein $R^3$ is, for example, methoxyl. The following diagram illustrates such schemes:

In Scheme I, the diazo starting material is available to the art. Typically, the first step of the reaction is conducted in a solvent medium such as ROH or a mixture of ROH and a solvent such as $CH_2Cl_2$, acetonitrile, or benzene or the like containing 1 to about 3 equivalents of a brominating agent such as N-bromoacetamide, N-bromosuccinimide, or the like; typically the reaction is conducted at from about $0°$ to about $50°$ C. for from a few minutes to 12 hours. The resulting 6-bromo- 6-$R^3$ species are known, as is the above described process species is then treated with a base (1.0 to 1.5 equivalents) such as an organo-metallic base, for example, n-butyl lithium, methyl magnesium bromide, or the like in a solvent such as diethyl ether, tetrahydrofuran, dimethoxyethane, or the like at a temperature of from $-80°$ C. to about $0°$ C.; and thereafter adding, as above-described, the reagent of choice

to give the desired final product.

The epoxide of Scheme II may be prepared by treatment of the olefin with an oxidizing agent such as hydrogen perioxide, or an organo peracid or directly from the 6-halo species by treatment with base. The resulting epoxide is then converted to the desired product by

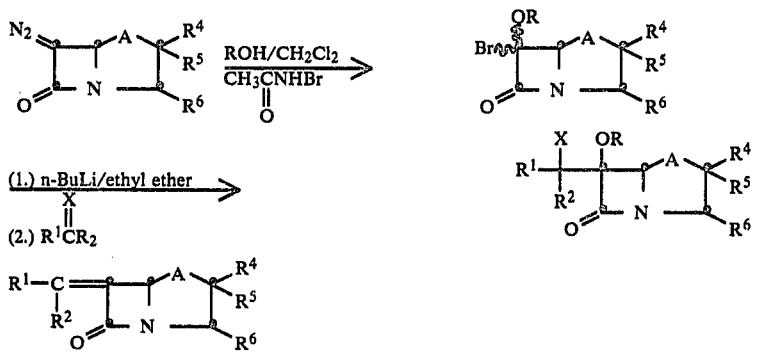

SCHEME I

SCHEME II

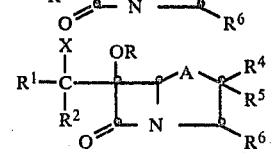

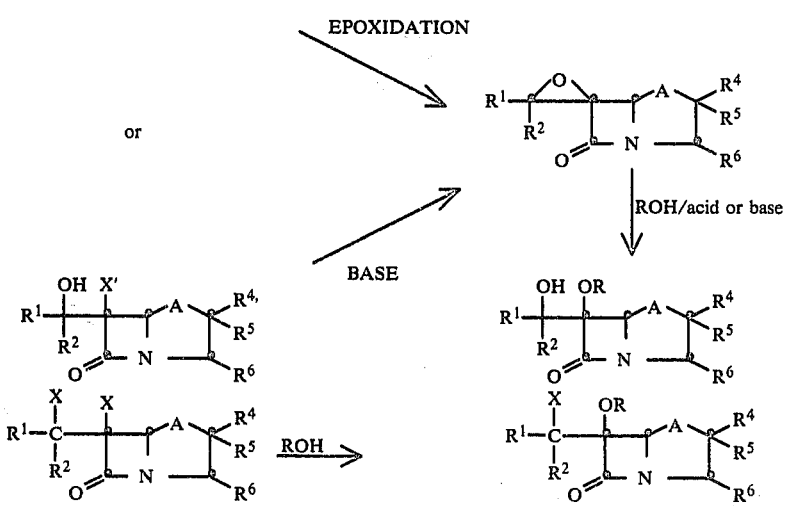

SCHEME III

With respect to the above Schemes I–III, all symbolism is as previously defined and ROH (which may also be RSH) designates a lower alkanol (or lower alkyl thio); thus in the final products —OR designates the substituent $R^3$.

treatment with ROH in the presence of acid or base. Suitable oxidizing agents are alkaline hydrogen peroxide or m-chloroperbenzoic acid. Typically the oxidation is conducted with m-chloroperbenzoic acid in a solvent such as methylene chloride, benzene, dioxane, or tetrahydrofuran at a temperature of from −20° C. to about 50° C. for from a few minutes to six hours. Direct conversion of the 6-halo species to the oxide is effected in solvents such as methanol, methylene chloride, acetonitrile and tetrahydrofuran in the presence of 1.0 to 2.0 equivalents of a base such as sodium methoxide, triethylamine, lithium diisopropylamide and sodium hydride at −20° C. to 50° C. for from a few minutes to six hours. Conversion of the oxide to the desired product is typically conducted in the alcohol of choice or in a mixture of the alcohol with a solvent such as methylene chloride, acetonitrile, benzene or tetrahydrofuran in the presence of a base (1 to 2 equivalents) such as sodium methoxide or triethylamine at −78° to 22° C. for from a few minutes to six hours. The oxide may be converted to the desired product by treatment in acidic solution. It is to be noted that the olefin starting material is known.

Scheme III is conducted by treating the 6-halo species in the alcohol of choice, for example methanol, ethanol, or a mixture of alcohol with some other solvent, as described above, with a reagent such as silver tetrafluoroborate at a temperature of from 0° to 50° C. for a few minutes to overnight.

The present invention embraces all stereoisomers of the compounds prepared by the above processes. However, it is well-know in the bicyclic β-lactam antibiotic art that certain isomers of a given species are more active than their corresponding enantiomorph. This appears to be true for the instant invention; although the extent of this relationship of antibiotic activity to configuration cannot be stated for all species embraced by the present invention. However, by way of illustration, the following relationship has been established for the species 6-(1-hydroxyethyl)penicillanic acid (I):

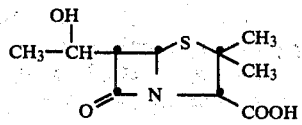

Because of the regio-specific synthesis, detailed above, there are only 4 stereoisomers of interest:

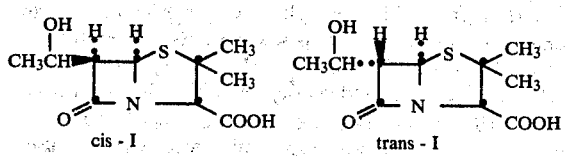

For each configuration, cis or trans, there are two stereoisomers. For example, relative to the cis configuration there are the following diastereomers:

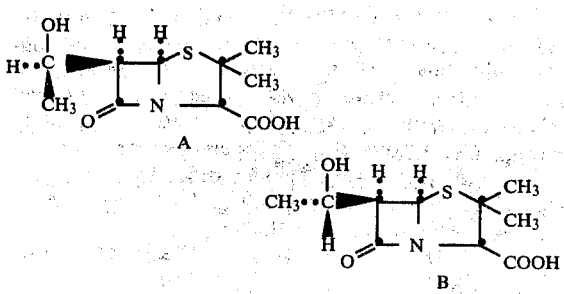

Correspondingly, there are two trans isomers. The absolute configuration of the isomers at the side chain carbon is not known; however, any given isomer may unambiguously be identified by physical parameters. In the specific case of the above-illustrated species all isomers appear active, however, the cis isomers designated A and B (above), are preferred as having higher activity.

Pharmaceutically acceptable salts which may be formed using procedures well known to the art from the compounds of the invention include (a) inorganic base salts such as alkali metal, e.g. sodium and potassium, alkaline earth, e.g. calcium, and organic base salts, e.g. procaine and dibenzylethylene diamine salts and (b) acid addition salts, e.g. with hydrochloric, hydrobromic, sulphuric, nitric, phosphoric, toluene-p-sulphonic and methanesulphonic acids. In addition to salts, the novel compounds of the present invention may be administered in the form of esters, including those discussed above. Examples of esters that might be mentioned are esters of alcohols, phenols, mercaptans, and thiophenols of the general formula —COOR$^8$ wherein R$^8$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(p-methylphenyl)ethyl, 2-(p-methylphenyl)sulfonylethyl, 2-methylaminoethyl, methylthioethyl, 2-chloro(or bromo)ethyl, benzyl, a substituted benzyl group such as p-nitrobenzyl, m-phenoxybenzyl, p-pivaloyloxybenzyl, benzyloxybenzyl, p-t-butylbenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl an acyloxy alkyl group such as acetoxymethyl, pivaloyloxymethyl, or ethyl, an alkoxy group such as methoxymethyl, aryloxymethyl such as phenoxymethyl, or a monocyclic aryl group for example phenyl or substituted phenyl such as p-nitrophenyl or 3,5-dinitrophenyl or unsaturated alkyl such as 3-methylbutenyl, methallyl, 3-butenyl, etc. These esters are readily prepared in accordance with processes well known in the art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus*. The compounds of the present invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats, emulsifying agents, for example lecithin, sorbitan monooleate or acacia; non-aqueous vehicles, which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being teated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10-60%. The composition will generally contain from about 15 mg. to about 1500 mg. by weight of active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

The following examples illustrate but do not limit the product, process, compositional or method of treatment aspects of the present invention.

EXAMPLE 1

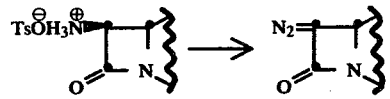

Preparation of Benzyl 6-Diazopenicillanate

A mixture of 20 g. (0.0419 mole) benzyl 6-aminopenicillante p-toluenesulfonic acid salt, 53 g. sodium nitrite, 900 ml. ice-cold methylene chloride and 900 ml. ice/water is combined and shaken in a 2 l. separatory funnel. p-Tolenesulfonic acid monohydrate (TsOH.H$_2$O) (8 g., 0.0420 mole) is added in three equal portions at 0,5 and 10 mins. The mixture is shaken almost constantly beginning at the first addition of TsOH.H$_2$O for 15 mins. The layers are separated and the aqueous fraction is washed with 100 ml. methylene chloride, which is added to the methylene chloride extract. The combined methylene chloride extracts are evaporated on a rotary evaporator at 25° C. to give a solution of benzyl 6-diazopenicillanate, which is used immediately for subsequent reactions.

EXAMPLE 2

Preparation of Benzyl-6,6-Dibromopenicillanate

To a stirred solution of freshly prepared benzyl diazopenicillanate (9.9 g., 31 mmol) in 300 ml. methylene chloride at −40° C. under nitrogen atmosphere is added dropwise a solution of bromine (5 g., 31 mmol) in 50 ml. methylene chloride over 55 minutes. The mixture is warmed to 0° over 45 minutes and evaporated under reduced pressure. The residue is purified by chromatography on silica gel to give 6.2 g. (44%) of product. Recrystallization from isopropanol gives m.p. 77.5°–79° (dec.); nmr (δ): 1.36, (3H,S); 1.6, (3H,S); 4.53, (1H,S); 5.16, (2H,S); 5.76, (1H,S); 7.33, (5H,S).

Analysis calcd. for: C$_{15}$H$_{15}$NO$_3$SBr$_2$: Calc.: C, 40.11; H, 3.37; N, 3.12; Br, 35.58. Found: C, 40.53; H, 3.37; N, 3.19; Br, 36.33.

EXAMPLE 3

Preparation of Benzyl 6-α-Iodopenicillanate

The methylene chloride solution containing benzyl 6-diazopenicillanate derived from 20 g. benzyl 6-aminopenicillanate p-toluenesulfonic acid salt (see previous Example) is evaporated to 150 ml. at 25° C. on a rotary evaporator and 1 l. acetone is added. The solution is stirred and cooled to 5° C. A solution of 25 g. sodium iodide and 16.4 ml. (57%) aqueous hydroiodic acid diluted to 125 ml. with ice and water is added to the stirred solution at a fast drip during 15 minutes. Internal temperature is maintained at 4° C.

After completion of addition the solution is stirred at 40° C. for 45 minutes, 25 g. solid sodium bicarbonate is added, and the slurry is stirred an additional 15 mins. at 4° C. The liquid is decanted and the residue is washed with acetone, which is added to the decantate. Evaporation provides a dark residue which is added to 100 ml. benzene. The combined organic fractions are washed with 100 ml. 5% aqueous sodium thiosulfate. The benzene solution is evaporated and the residue is chromatographed on 250 g. Baker silica gel with benzene as eluant.

The product obtained, benzyl 6-α-iodopenicillanate, weighs 9.9 g. (56.5%) and its identity is confirmed by NMR spectral analysis.

EXAMPLE 4

Preparation of Benzyl 6-α-Bromopenicillanate

Following the procedure of Example 3, benzyl 6-α-bromopenicillanate is obtained in 59% yield when the NaI/HI of Example 3 is replaced by an equivalent amount of NaBr/HBr.

EXAMPLE 5

Preparation of benzyl 6-bromo-6-(hydroxyethyl)penicillanate

To a stirred solution of benzyl 6,6-dibromopenicillanate (3.5 g., 7.75 mmoles) in 80 ml. of anhydrous tetrahydrofuran at −70° C. under nitrogen atmosphere is added dropwise 3.25 ml. of a 2.38 M solution of butyllithium in hexane. The mixture is stirred for 10 minutes and a solution of acetaldehyde (0.36 g., 8.25 mmoles) in 2.4 ml. of anhydrous tetrahydrofuran is added. The resulting mixture is stirred at −70° C. under nitrogen atmosphere for 15 minutes and the reaction is then quenched with 10.0 ml. of a saturated, aqueous ammonium chloride solution. The cold solution is filtered and the filtrate is concentrated under reduced pressure. The concentrate is partitioned between chloroform and aqueous brine (NaCl) and the organic phase is separated, dried with magnesium sulfate, filtered, and evaporated. The residue is purified by chromatography on silica gel with benzene-ethyl acetate (6:1) to give 1.3 g. (41%) of a mixture of diastereomers of both benzyl 6-α-bromo-6-β-(hydroxyethyl) and benzyl 6-β-bromo-6-α-(hydroxyethyl)penicillanates.

Separation of this material into a single diastereomer and a pair of isomers is accomplished on silica gel eluting with methylene chloride-ethyl acetate (100:1). The single, non-polar diastereomer is characterized spectroscopically:IR (CHCl$_3$):3600–3200 cm$^{-1}$, 1783 cm$^{-1}$, and 1748 cm$^{-1}$; nmr (CDCl$_3$):1.23δ(3H,d,J=6Hz); 1.4, (3H,S); 1.61, (3H,S); 2.66, (1H,bs); 3.95–4.41, (1H,m); 4.53, (1H,s); 5.19, (2H,s); 5.56, (1H,s); and 7.35, (5H,s); mass spec.: M$^+$=415, 413, 334, 250, 225, 223, 166, 164, 114, 91.

The more polar isomeric pair is characterized analogously: IR (CHCl$_3$) 3600–3200 cm$^{-1}$, 1783 cm$^{-1}$, and 1748 cm$^{-1}$; nmr (CDCl$_3$): 1.36δ(3H,s); 1.46, (3H,d,J=6 Hz); 1.6, (3H,s); 2.76, (1H,bs); 3.93–4.43, (1H,m); 4.46, (1H,s); 5.16; (2H,s); 5.46 and 5.48, (1H,s); and 7.33, (5H,s); mass spec: M$^+$=415,413; 334, 250,225, 223, 166, 164, 114, 91.

EXAMPLE 6

Preparation of benzyl 6-β-(1-hydroxyethyl)-penicillanate (Isomer (3))

To a stirred suspension of excess zinc-silver couple in 1.0 ml. of methanol at room temperature is added in rapid succession 75.6 mg. (1.26 mmole) of glacial acetic acid and a solution of 197.7 mg. (0.48 mmole) of the more polar, isomeric pair of bromohydrins in 1.0 ml. methanol. The mixture is stirred under nitrogen atmosphere for 5 minutes and the excess zinc-silver couple removed by filtration. The filtrate is evaporated and the residue obtained is partitioned between ethyl acetate and dilute, aqueous hydrochloric acid. The organic phase is separated and is washed successively with brine solution (aqueous NaCl) and dilute, aqueous sodium bicarbonate solution, and is dried with magnesium sulfate, filtered, and evaporated. Purification by preparative thin layer chromatography on silica gel affords 76 mg. (48%) of a mixture of both benzyl 6-α-(hydroxyethyl)penicillanate diastereomers and a single diastereomer of benzyl 6-β-(hydroxyethyl)penicillanate.

EXAMPLE 7

Preparation of benzyl 6-(1-hydroxyethyl)penicillanate as a mixture of diastereomers To a stirred solution of 2 g. benzyl 6-α-iodopenicillanate (4.82 mmoles) in 50 ml. ethyl ether under nitrogen cooled to −73° C. in Dry Ice/isopropanol is added 2 ml. of 2.4 M n-butyllithium in hexane (4.82 mmoles). A white precipitate forms rapidly. The mixture is stirred at −73° C. for 20 minutes and acetaldehyde (0.5 ml., 85% excess) is added. Dry tetrahydrofuran (1 ml.) is added to the reaction mixture at 2, 20 and 30 minutes. After 5 minutes additional stirring at −73° C., the reaction flask is moved to a −40° C. bath in which it is stirred well for 30 minutes. Saturated aqueous ammonium chloride (10 ml.) is added and the mixture is stirred well for 5 minutes. Layers are separated and the aqueous layer is washed well with methylene chloride. The combined organic layers are dried and evaporated to give a residue of 2.0 g.

The residue is chromatographed on 150 g. Baker silica gel using ethyl acetate (10–30%) in benzene as eluant. The product benzyl 6-(1-hydroxyethyl)penicillanate, 1.61 g., 50% yield, is obtained as a mixture of diastereomers and its identity is confirmed by nmr spectral analysis.

In the above procedure other reagents may be substituted for acetaldehyde and analogous products obtained: when acetone is substituted for acetaldehyde, benzyl 6-(2-hydroxy-2-propyl)penicillanate is obtained; when phenylacetaldehyde is substituted for acetaldehyde, benzyl 6-(1-hydroxy-2-phenylethyl)penicillanate is obtained.

EXAMPLE 8

Analysis and separation of diastereomeric benzyl 6-(1-hydroxyethyl)penicillanates Mixtures of diastereomic compounds are obtained by the procedures described above. Analytical procedures are available for their separation and identification. Preparative procedures are also available for separation of the diastereomers on a preparative scale.

Mixtures of the diastereomers are analyzed by gas chromatography of the corresponding trimethylsilyl derivatives. These derivatives are prepared by treating a 1 mg. sample of the mixture with 2 drops of dry dimethylformamide and 2 drops of bis-(trimethylsilyl)trifluoroacetamide. After 10 minutes at 22° C., the reaction solution is analyzed directly—typically with 5'×⅛" column of 5% SE-30 on 100/120 mesh Varaport in a Varian gas chromatograph at 220° C., where individual peaks are seen for the diastereomers.

Mixtures of the diastereomers are separable by high pressure liquid chromatography, typically with a Waters Associates, Inc. model ALC/GPC 244 liquid chromatograph using Porosil A column packing and 1½% acetonitrile in chloroform as eluant. The technique of peak shaving and recycling is advantageously employed to achieve separation.

In this manner the four diastereomeric benzyl (6-(1-hydroxyethyl)penicillantes are separable. The compounds obtained are identifiable by NMR spectral analysis.

EXAMPLE 9

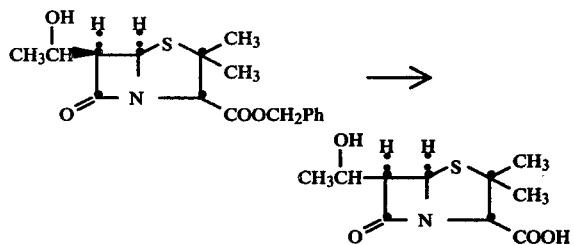

Preparation of 6-(1-hydroxyethyl)penicillanic acid (isomer 4) From its benzyl ester To a stirred mixture of 150 mg. 10% Pd on C in 10 ml. methanol, 2 ml. water and 1 ml. of 0.1 N phosphate buffer (pH=7.0), which is pre-reduced with hydrogen at atmospheric pressure, is added 37 mg. of benzyl 6-(1-hydroxyethyl)penicillanate in 3 ml. methanol. Uptake of hydrogen ceases in 10 minutes and the reaction is stirred for an additional 20 minutes.

The catalyst is removed by filtration and washed well with methanol. The combined filtrate and washings are evaporated under reduced pressure and the residue is diluted to 15 ml. with water. The pH is adjusted to 8.5 with saturated aqueous sodium bicarbonate and the solution is extracted with 15 ml. ethyl acetate. The aqueous solution is adjusted to pH 3 with 2.5 N hydrochloric acid and extracted with 2×25 ml. ethyl acetate.

The combined ethyl acetate extract is dried with anhydrous magnesium sulfate, filtered and evaporated to afford 18.8 mg. of crystalline acid, m.p. 150° C. The product is identified by its NMR spectrum and analyzed by gas chromatography of the ditrimethylsilyl derivative prepared as described above for preparation of the monosilyl derivative of the corresponding benzyl ester.

In similar fashion other ester isomers (such as benzyl) of the same gross structure may be converted to the corresponding free acids by the above procedure.

Also, analogues of the 6-(1-hydroxyethyl)compounds may be converted from their esters to their corresponding free acid in a similar manner.

In this fashion the other three isomers of the diastereomeric 6-(1-hydroxyethyl)penicillanic acids are prepared from the corresponding benzyl esters.

In the same manner other ester analogues may be converted to the corresponding penicillanic acids.

EXAMPLE 10

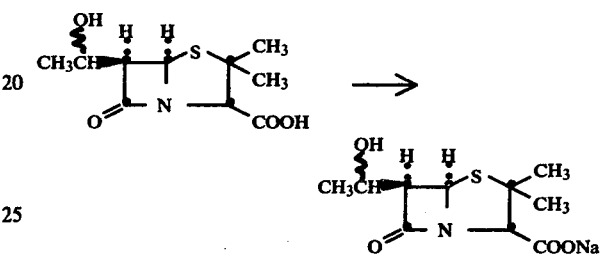

Preparation of 6-(1-hydroxyethyl)penicillanic acid sodium salt (isomer 4)

A sample of 15.1 mg. of 6-(1-hydroxyethyl)penicillanic acid isomer 4 is dissolved in 2 ml. acetone and 2 ml. water and 5.3 mg. solid sodium bicarbonate is added. After solution occurs the sample is concentrated under reduced pressure and lyophilized in vacuo providing 19.8 mg. of 6-(1-hydroxyethyl)penicillanic acid sodium salt isomer 4.

Other benzyl esters including the remaining three diastereomeric 6-(1-hydroxyethyl)penicillanates as well as benzyl ester analogs may be deblocked to free penicillanic acids and then converted to the corresponding sodium salts by the procedures described above.

EXAMPLE 11

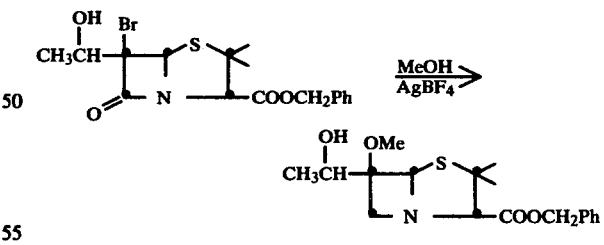

Preparation of Benzyl 6-methoxy-6-(1-hydroxyethyl)penicillanate

To a stirred solution of 1.0 g. (2.46 mmoles) of benzyl 6-bromo-6-(1-hydroxyethyl)penicillante in 20 ml. of methanol under nitrogen at 22° C. is added 0.48 g. (2.46 mmoles) of silver tetrafluoroborate. Progress of the reaction is followed by thin layer chromatography. When the reaction is complete the solution is evaporated under reduced pressure and the residue is purified by column chromatography on silica gel using mixtures of benzene and ethyl acetate.

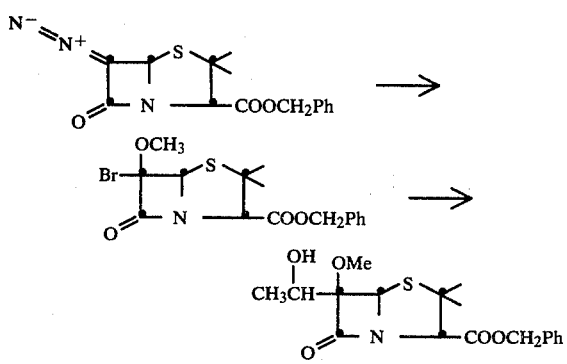

Preparation of benzyl 6-methoxy-6-(1-hydroxyethyl)penicillanate

Benzyl 6-methoxy-6-bromopenicillanate [prepared according to L. D. Cama, W. J. Leanza, T. R. Beattie and B. G. Christensen, J. Am. Chem. Soc., 95, 1408 (1972)] is treated with n-butyllithium followed by acetaldehyde according to the procedure of Example 5 to provide benzyl 6-methoxy-6-(1-hydroxyethyl)penicillanate.

by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-$\beta$-(1-hydroxyethyl)penicillanic acid | 125 mg. |
| Dicalcium Phosphate | 192 mg. |
| Cornstarch, U.S.P. | 6 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION

Ampoule:

| Compound | $R^1$ | $R^2$ | $R^3$ | A | $R^4$ | $R^5$ | $R^6$ | X |
|---|---|---|---|---|---|---|---|---|
| 1 | H | H | H | S | $CH_3$ | $CH_3$ | $COOCH_2Ph$ | OH |
| 2 | $PhCH_2CH_2-$ pH = phenyl | H | H | S | $CH_3$ | $CH_3$ | $COOCH_2Ph$ | OH |
| 3 | H | H | $OCH_3$ | S | $CH_3$ | $CH_3$ | $COOCH_2Ph$ | OH |
|  | $CF_3$ | H | H | S | $CH_3$ | H | COOTMS TMS = trimethylsilyl | OH |
| 4 | $NH_2$ \| $PhCHCH_2$ | H | H | O | H | H | $COO-\langle\rangle-NO_2$ | OH |
| 5 | $CH_3$ | — | H | S | $CH_3$ | $CH_3$ | COOTMS | =O |
| 6 | H | H | H | O | H | H | $COOCH_2Ph$ | OH |
| 7 | HOOC-$\langle\rangle$-$CH_2CH_2$ | $CH_3$ | H | S | $CH_3$ | $CH_3$ | COOTMS | OH |
| 8 | $CH_3$ | — | H | S | $CH_3$ | $CH_3$ | $COOCH_2Ph$ | =NH |
| 9 | $CH_3$ | H | H | S | $CH_3$ | $CH_3$ | $COOCH_3Ph$ | $-NH_2$ |
| 10 | $\langle\rangle$-$CH_2CH_2CH_2$ | H | H | S | $CH_3$ | $CH_3$ | $COOCH_2Cl_3$ | OH |
| 11 | $CH_3$ | H | H | S | $CH_3$ | $CH_3$ | COOTMS | SH |
| 12 | $CH_3$ | H | H | S—O | $CH_3$ | $CH_3$ | $COOCH_2Ph$ | OH |
| 13 | $CH_3$ | H | H | $NCH_3$ | $CH_3$ | $CH_3$ | $COOCH_2Ph$ | OH |
| 14 | $CH_3$ | $CH_3$ | H | S | $CH_3$ | $CH_3$ | $COOCH_2Ph$ | OH |
| 15 | $PhCH_2$ | H | H | S | $CH_3$ | $CH_3$ | $COOCH_2Ph$ | OH |
| 16 | $PhCHCH_2$ \| $CO_2H$ | H | H | S | $CH_3$ | $CH_3$ | $COOCH_2Ph$ | OH |
| 17 | $CH_3CH_2$ | H | H | S | $CH_3$ | $CH_3$ | $COOCH_2Ph$ | OH |
| 18 | PhCH \| $NH_2$ | H | H | S | $CH_3$ | $CH_3$ | $COOCH_2Ph$ | OH |
| 19 | $CH_3$ | H | H | $CH_2$ | H | H | $COOCH_2Ph$ | OH |

EXAMPLE 13

Preparation of Pharmaceutical Compositions

One such unit dosage form consists in mixing 120 mg. of 6-$\beta$-(1-hydroxyethyl)penicillanic acid with 20 mg. of lactose and 5 mg. of magnesium stearate and placing the 145 mg. mixture into a No. 3 gelatin capsule. Similarly, 6-$\beta$-(1-hydroxyethylpenicillanic acid: 500 mg.
Diluent: Sterile Water for Injection: 2 cc.

OPTHALMIC SOLUTION

6-$\beta$-(1-hydroxyethyl)penicillanic acid: 100 mg.

Hydroxypropylmethyl Cellulose: 5 mg.
Sterile Water: to 1 ml.

OTIC SOLUTION

6-β-(1-hydroxyethyl)penicillanic acid: 100 mg.
Benzalkonium Chloride: 0.1 mg.
Sterile Water: to 1 ml.

TOPICAL OINTMENT

6-β-(1-hydroxyethyl)penicillanic acid: 100 mg.
Polyethylene Glycol 4000 U.S.P.: 400 mg.
Polyethylene Glycol 400 U.S.P.: 1.0 gram The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound of the structural formula:

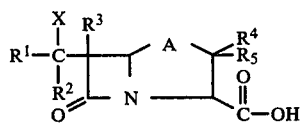

and the non-toxic pharmaceutically acceptable salts thereof wherein:

A is S, SO, or $NR^7$;
$R^7$ is hydrogen, $C_{1-6}$ lower alkyl or $C_{1-6}$ lower alkanoyl;
$R^4$ and $R^5$ are independently selected from hydrogen and methyl;
$R_3$ is hydrogen, methoxyl, halo or methylthio;
X is OH, =O, SH, =NH, $NH_2$ or $NHR^7$; and $R^1$ and $R^2$ are independently selected from hydrogen, substituted and unsubstituted $C_{1-6}$ lower alkyl, benzyl, phenylethyl, phenylpropyl and thienylmethyl; wherein the ring or chain substituent relative to $R^1$ and $R^2$ are selected from carbonyl, amino and hydroxyl; with the proviso that when X is =O or NH, the substituent $R^2$ is absent.

2. A compound of claim 1 wherein:
A is S;
X is OH;
$R^1$ and $R^2$ are independently selected from hydrogen, loweralkyl, benzyl, phenylethyl or phenylpropyl; and
$R^3$ is hydrogen or methoxyl.

3. An antibiotic pharmaceutical composition comprising a therapeutically effective amount, in unitary dosage form, of a compound according to claim 1 and a pharmaceutical carrier therefore.

* * * * *